(12) United States Patent
Hartman et al.

(10) Patent No.: US 9,770,552 B2
(45) Date of Patent: Sep. 26, 2017

(54) INFRARED REFLECTIVE AIR-IN-LINE SENSOR SYSTEM

(75) Inventors: Adam Hartman, Denton, TX (US); Paul Nguyen, Plano, TX (US); David Charles Cummings, Richardson, TX (US)

(73) Assignee: Nestec S.A., Vevey (CH)

( * ) Notice: Subject to any disclaimer, the term of this patent is extended or adjusted under 35 U.S.C. 154(b) by 714 days.

(21) Appl. No.: 14/234,768

(22) PCT Filed: Jul. 9, 2012

(86) PCT No.: PCT/EP2012/063412
§ 371 (c)(1),
(2), (4) Date: Jan. 24, 2014

(87) PCT Pub. No.: WO2013/013966
PCT Pub. Date: Jan. 31, 2013

(65) Prior Publication Data
US 2014/0155865 A1    Jun. 5, 2014

(51) Int. Cl.
*A61M 5/168* (2006.01)
*A61M 5/142* (2006.01)
*A61M 5/36* (2006.01)
*G01N 21/41* (2006.01)
*A61J 15/00* (2006.01)
(Continued)

(52) U.S. Cl.
CPC ...... *A61M 5/16831* (2013.01); *A61J 15/0026* (2013.01); *A61M 5/14228* (2013.01);
(Continued)

(58) Field of Classification Search
CPC ............ A61M 1/3626; A61M 5/16831; A61M 5/365; A61M 38/08–2039/087;
(Continued)

(56) References Cited

U.S. PATENT DOCUMENTS

| 4,559,454 A | 12/1985 | Kramer |
| 4,762,518 A | 8/1988 | Kreinick |

(Continued)

FOREIGN PATENT DOCUMENTS

| EP | 0341364 | 11/1989 |
| WO | 9702059 | 1/1997 |

(Continued)

*Primary Examiner* — Bhisma Mehta
*Assistant Examiner* — Larry R Wilson
(74) *Attorney, Agent, or Firm* — K&L Gates LLP (57) ABSTRACT

Air-in-line sensor systems and methods of using same are provided. The system includes an adapter (60) including first and second cylindrical portions defining a fluid flow channel, the first cylindrical portion comprising two adjacent wedge-shaped protrusions (68). Each wedge-shaped protrusion is infrared transmittive and defines an outer surface and an inner surface. The system further includes a tube and an infrared reflective sensor having an infrared light emitter (42,52) and an infrared light detector (44,54). The infrared light emitter and the infrared light detector are positioned at or near an adapter so that an infrared light can be transmitted to the adapter and at least a portion of the infrared light reflected off the adapter can be detected by the infrared light detector.

19 Claims, 4 Drawing Sheets

(51) Int. Cl.
*G01N 21/05* (2006.01)
*G01N 21/47* (2006.01)
*G08B 21/18* (2006.01)

(52) U.S. Cl.
CPC ........ *A61M 5/14232* (2013.01); *A61M 5/365* (2013.01); *G01N 21/05* (2013.01); *G01N 21/41* (2013.01); *G01N 21/47* (2013.01); *G08B 21/182* (2013.01); *A61M 2205/12* (2013.01); *A61M 2205/18* (2013.01); *A61M 2205/3306* (2013.01); *A61M 2205/3313* (2013.01)

(58) Field of Classification Search
CPC ........ A61M 2039/16; A61M 2039/167; A61M 2205/12; A61M 2205/18; A61M 2205/3306; A61M 2205/331; A61M 2205/3313; A61J 15/0026; G01N 21/05; G01N 21/41; G01N 21/47; G01N 2021/052

See application file for complete search history.

(56) References Cited

U.S. PATENT DOCUMENTS

| | | | |
|---|---|---|---|
| 5,644,402 A * | 7/1997 | Chevallet | A61M 1/1692 250/559.4 |
| 5,672,887 A | 9/1997 | Shaw et al. | |
| 5,853,386 A * | 12/1998 | Davis | A61M 5/16854 128/DIG. 13 |
| 8,094,307 B2 * | 1/2012 | Slepicka | A61M 1/28 356/364 |
| 2008/0098798 A1 * | 5/2008 | Riley | A61M 5/365 73/19.03 |
| 2010/0241062 A1 | 9/2010 | Morris et al. | |
| 2012/0172800 A1 | 7/2012 | Dudar et al. | |

FOREIGN PATENT DOCUMENTS

| | | |
|---|---|---|
| WO | 9804301 | 2/1998 |
| WO | 2009027896 | 3/2009 |

* cited by examiner

INFRARED REFLECTIVE AIR-IN-LINE SENSOR SYSTEM

CROSS REFERENCE TO RELATED APPLICATIONS

The present application is a National Stage of International Application No. PCT/EP12/063412 filed on Jul. 9, 2012, which claims priority to U.S. Non-Provisional application Ser. No. 13/190,155, filed on Jul. 25, 2011, the entire contents of which are incorporated herein by reference.

BACKGROUND

The present disclosure generally relates to health and nutrition. More specifically, the present disclosure relates to devices and methods for detecting air in the tubing set of fluid pump systems.

The delivery of nutritional compositions to mammals, such as human patients, that cannot orally ingest food or other forms of nutrition is often of critical importance. For example, enteral bottles and containers having feeding tubes that deposit food directly into the gastrointestinal tract at a point below the mouth are often used to sustain life while a patient is unable, or refuses, to take food orally. Bottles and containers, feeding tubes and other artificial delivery systems and routes can be used temporarily during the treatment of acute medical conditions. For chronic medical conditions, such systems and routes can be used as part of a treatment regimen that lasts for the remainder of a patient's life. No matter the duration of use, these devices often provide the only means for feeding and, thus, nutrient supply, for the patient.

The use of enteral feeding pumps, in conjunction with an enteral feeding tube set as part of an enteral feeding system, for the administering of medical fluids is also well known in the medical arts. The enteral feeding tube set will typically include several long sections of tubing, connected to a centralized, shorter section of tubing that can be incorporated into a pumping device. One common concern with the enteral feeding tube set is that it may contain air boluses (e.g., bubbles), that can cause bloating, pain or general discomfort during and/or after feedings.

SUMMARY

The present disclosure relates to air-in-line sensor systems and methods of using the air-in-line sensor systems. In a general embodiment, the present disclosure provides an adapter device having first and second cylindrical portions defining a fluid flow channel. The fluid flow channel extends through both the first and second cylindrical portions. The first cylindrical portion includes two adjacent wedge-shaped protrusions. In an embodiment, each wedge-shaped protrusion having at least a portion that is infrared transmittive and each protrusion defining an outer surface and an inner surface. The inner surfaces of the wedge-shaped protrusions may define a substantially triangularly shaped recess.

In an embodiment, the adapter has an interior surface defining a hollow interior that is so constructed and arranged to allow fluid to flow therethrough. At least a portion of the interior surface of the adapter may be flat and infrared reflective. In another embodiment, at least a portion of the interior surface of the adapter may be infrared transmissive.

In an embodiment, the adapter is manufactured from polypropylene.

In another embodiment, a cassette is provided and includes a rigid frame, a tube, and at least one adapter having first and second cylindrical portions defining a fluid flow channel. The first cylindrical portion includes two adjacent wedge-shaped protrusions. In an embodiment, each wedge-shaped protrusion having at least a portion that is infrared transmittive and each protrusion defining an outer surface and an inner surface. The inner surfaces of the wedge-shaped protrusions may define a substantially triangularly shaped recess.

In an embodiment, the at least one adapter is located on a first end of the cassette.

In an embodiment, the first portion of the adapter is configured to mate with the tube. The second portion of the adapter may be configured to mate with a second tube.

In an embodiment, the cassette includes first and second adapters, the first adapter is located on a first end of the cassette and the second adapter located on a second end of the cassette.

In yet another embodiment, a sensor system is provided and includes a pumping device and a cassette removably attached to the pumping device. The pumping device includes at least one infrared reflective sensor having an infrared light emitter and an infrared detector. The cassette includes a tube and at least one adapter having first and second cylindrical portions defining a fluid flow channel. In an embodiment, each wedge-shaped protrusion having at least a portion that is infrared transmittive and each protrusion defining an outer surface and an inner surface. The inner surfaces of the wedge-shaped protrusions may define a substantially triangularly shaped recess. The infrared reflective sensor is positioned so that an infrared light can be transmitted through the outer surface of a first wedge-shaped protrusion and at least a portion of the infrared light reflected off an inner surface of the first cylindrical portion can be detected by the infrared detector.

In an embodiment, the pumping device is an enteral feeding pump.

In an embodiment, the infrared light emitter and the infrared detector are positioned on the same side within the pumping device. In another embodiment two infrared sensors are provided, one on each end of the pumping device. The infrared light emitter and the infrared detector may also be located on a bottom, interior portion of the pumping device such that the infrared light emitter emits the infrared light in an upward direction. The at least one adapter may be located on an end of the cassette and is configured such that the first and second adjacent wedge-shaped protrusions are oriented downward to communicate with the infrared light emitter and the infrared detector.

In still yet another embodiment, a method of detecting air in a tubing set for an enteral feeding system is provided. The method includes the steps of providing a cassette having an adapter sealingly attached to an enteral feeding tube, and detecting air within the enteral feeding tube. The adapter includes first and second portions defining a fluid flow channel. The first portion includes two adjacent wedge-shaped protrusions, each wedge-shaped protrusion having at least a portion that is infrared transmittive and each protrusion defining an outer surface and an inner surface. The detecting occurs by transmitting an infrared light to the outer surface of the first wedge-shaped protrusion and detecting an amount of reflected infrared light using a detector.

In an embodiment, the infrared light is transmitted through the outer surface of a first wedge-shaped protrusion, and the reflected infrared light passes through the outer surface of a second wedge-shaped protrusion.

In an embodiment, the method further includes inserting the cassette into a pumping device to administer an enteral feeding to a patient.

In an embodiment, the method further includes stopping an enteral feeding cycle if air is detected in the enteral feeding tube. Alternatively, the method may include sounding an audible alarm if a threshold amount of air is detected in the enteral feeding tube.

An advantage of the present disclosure is to provide an improved in-line sensor for detecting air in a tubing set.

Another advantage of the present disclosure is to provide an improved method for detecting air in a tubing set for enteral feeding.

Yet another advantage of the present disclosure is to provide an improved sensor for detecting air that is cost-effective.

Still another advantage of the present disclosure is to provide an improved sensor for detecting air that is simple to operate.

Another advantage of the present disclosure is to provide an adapter that can be used to detect air in a tubing set for enteral feeding.

Yet another advantage of the present disclosure is to provide a cassette having an adapter that can be used to detect air in a tubing set for enteral feeding.

Additional features and advantages are described herein, and will be apparent from the following Detailed Description and the figures.

DETAILED DESCRIPTION

Enteral feeding pumps are devices that control the timing and the amount of nutrition delivered to a patient during enteral feeding. Enteral feeding is the administration of nutrient fluids to a patient who cannot eat via normal ingestion routes. Enteral administration typically occurs through a set of tubes between a feeding sack and a catheter implanted to the patient. A disposable cassette typically carries at least a portion of the tubing so that spent tubing may be easily disposed of. An enteral feeding pump is usually connected to the feeding sack with one tube from a first side and with another tube to the patient on a second side.

Due to the nature of the enteral fluids, the administering process and other enteral feeding conditions, it may occur that an amount of air is administered instead of feeding fluid, which can easily result in discomfort or pain to the patient. A typical example of this issue occurs when the nutrient food sack becomes empty. If the enteral pump continues the administration, air is pumped through the tubing to the patient instead of food.

The present disclosure is directed to a sensor system that is able to sense the presence of air instead of nutrient fluid in the tubes of the enteral feeding system. When the volume of the pumped air has reached a programmed threshold, an alarm may be sent to the user. The sensor system is also able to distinguish between a small air bubble and the presence of the determined amount of air in the tube, thereby avoiding false alarms to the user.

The detection of the presence and amount of air in the tubing is based on the total internal reflection ("TIR") principle derived from Snell's Law and the Fresnel Equations, which specify the relative amount of light reflected and transmitted by a surface. The Law and the Equations describe the behavior of a beam of light when it passes the surface between two media characterized by different refraction indices.

Figure 1:
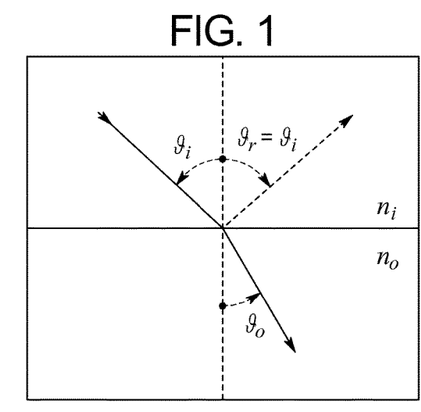
FIG. 1 shows light passing from a first medium to a second medium having a higher index of refraction.

Snell's Law describes the physical principle when a ray of light passes from one medium to another. Specifically, Snell's Law states that the ratio of the sine of the angle of incidence to the sine of the angle of refraction is constant. The constant is either equal to (i) the ratio of phase velocities ("v") in the two media, or (ii) the opposite ratio of the indices of refraction ("n") of the two media. Thus, Snell's Law is represented graphically by FIG. 1, and may be summarized as follows:

$$\frac{\sin\vartheta_i}{\sin\vartheta_o} = \frac{v_i}{v_o} = \frac{n_i}{n_o} \qquad \text{Equation 1}$$

In Equation 1, $\theta_i$ is the ray incidence angle, $\theta_o$ is the refracted angle, $\theta_r$ is the reflected angle, $v_i$ and $v_o$ are the phase velocities of the two materials, and $n_i$ and $n_o$ are the refraction indexes of the two materials.

Based on the possible values of the out-going ray angle, the following inequality, derived by Equation 1, shall be verified:

$$\sin\vartheta_o = \frac{n_i}{n_o}\sin\vartheta_i \leq 1 \qquad \text{Equation 2}$$

When light passes from a first medium to a second medium characterized by an higher refraction index, the beam of light reduces its angle to the normal at the surface of separation between the two media, as illustrated in FIG. 1. As is also shown in FIG. 1, an amount of partial reflection also occurs.

Figure 2:
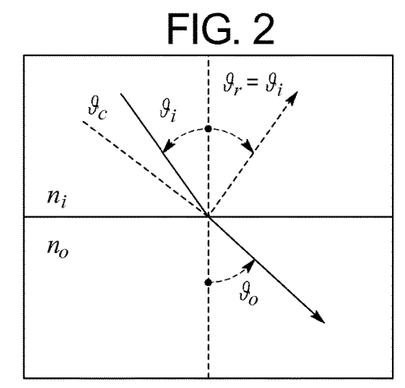
FIG. 2 shows light passing from a first medium to a second medium having a lower index of refraction.

In another example, when light passes from a first medium to a second medium characterized by a lower refraction index, the beam of light increases its angle to the normal at the surface of separation between the two media and an amount of partial reflection also occurs, as illustrated in FIG. 2. In this situation (where light passes from a first medium to a second medium characterized by a lower refraction index), when the ratio of the refraction indices is fixed and ≥1, the sine of the incoming angle can only assume the values satisfying the following inequality:

$$\sin\vartheta_i \le \frac{n_o}{n_i} \qquad \text{Equation 3}$$

With respect to Equation 3, when $$\sin\vartheta_i < \frac{n_o}{n_i},$$

both refraction and partial reflection will occur. When $$\sin\vartheta_i = \frac{n_o}{n_i}, \vartheta_o = \frac{\pi}{2}$$

and $\theta_t$ is the critical angle. When $$\sin\vartheta_i > \frac{n_o}{n_i}$$

refraction cannot occur and TIR occurs.

Figure 3:
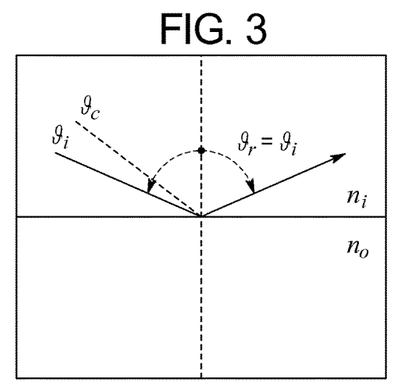
FIG. 3 shows total internal reflection of an incident light ray.

By increasing the incidence angle, the refraction angle also increases, and approaches a point in which the refracted beam runs parallel to the surface separating the two media. This incident angle is called the "critical angle." Further, when increase of the incident angle cannot result in refraction, TIR occurs instead, as illustrated in FIG. 3. The word "total" is important because, in contrast to FIGS. 1 and 2, in which some amount of light is reflected and some is refracted, when TIR occurs, all of the energy of the incident beam of light is reflected back.

The critical angle, thus, is defined as the arc whose sin equates the ratio between the refraction index of the outgoing ray and the incident ray. In terms of a mathematical equation, the critical angle is defined as follows:

$$\arcsin\vartheta = \frac{n_o}{n_i} \qquad \text{Equation 4}$$

As an example, the critical angle from water to air is about 48.6° and is represented by $\theta_c$ in FIGS. 2 and 3. As shown in FIG. 2, $\theta_i$ is lower than $\theta_c$ so partial reflection and refraction occur. As shown in FIG. 3, $\theta_i$ is greater than $\theta_c$ so TIR occurs. Thus, with the same critical angle, which is related to the refraction index of the two materials, different incident angles cause different paths of the incident rays.

Figure 4:
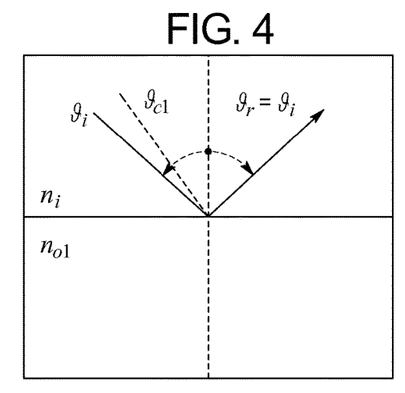
FIG. 4 shows an incident light ray having an angle that is lower than the critical angle.
Figure 5:
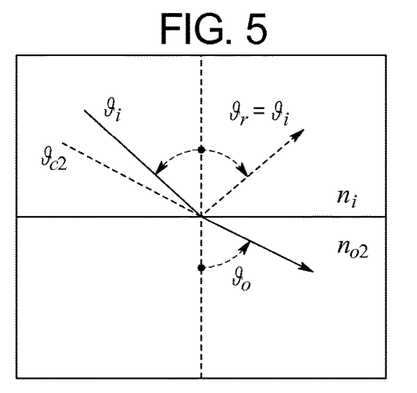
FIG. 5 shows an incident light ray having an angle that is greater than the critical angle.

In another example, the incident angles remain the same but the nature of the second material changes, thus also changing the refraction index. As shown in FIG. 4, $\theta_{c1}$ is lower than $\theta_i$ so TIR occurs. As shown in FIG. 5, $\theta_{c2}$ is greater than $\theta_i$ so partial reflection and refraction occurs. Thus, with the same incident angle, different amounts of light can be reflected, given the refraction index of the second material.

In other words, it is possible to distinguish different materials measuring the amount of light received at the reflection surface of the first material. For example, assuming that food has a refraction index similar to that of water and other effects of lower order such as scattering, ambient light, sticky food, etc. are not present or are mitigated, a TIR situation may be adopted to determine the present of, for example, air in the tubing of an enteral pump.

Accordingly, Snell's Law provides a method by which the refraction angles and the critical angles may be determined, given the incidence angle and the refraction indices of the two media. Using the same data, the Fresnel Equations allow the relative amount of light reflected with respect to the amount of light transmitted to be determined. For example, with reference to FIGS. 4 and 5, the Fresnel Equations can provide the amount of light reflected and the amount of light transmitted. A precise determination of these values is important because it can aid in clearly distinguishing, for example, the presence of air or food in the tubing of an enteral pump.

Referring again to FIG. 1, the fraction of the incident power that is reflected is given by the reflectance ("R") and the fraction that is refracted is given by the transmittance ("T"). The calculations of R and T depend on the polarization of the incident ray. Considering s-polarized light (perpendicular to the plane of FIG. 1) and p-polarized light (in the plane of FIG. 1), the R and T coefficients are given by the following:

$$R_s = \left(\frac{n_i \cos\vartheta_i - n_o \cos\vartheta_o}{n_i \cos\vartheta_i + n_o \cos\vartheta_o}\right)^2 \qquad \text{Equation 5}$$
$$T_s = 1 - R_s$$

$$R_p = \left(\frac{n_i \cos\vartheta_o - n_o \cos\vartheta_i}{n_i \cos\vartheta_o + n_o \cos\vartheta_i}\right)^2 \qquad \text{Equation 6}$$
$$T_p = 1 - R_p$$

If the incident light is unpolarized, the reflection coefficient is:

$$R = \frac{(R_s + R_p)}{2}$$

Applicants have now found that properly choosing a material for the first medium, the geometry around the surface between the two media, the incident angle, and the way to generate and sense the light, it is possible to design a sensor able to distinguish if the second medium is, for example, air or fluid. For example, if the first medium has a refraction index of 1.5, the refraction index of air is 1, and that of water is 1.33, any incidence angle between about 42° and about 62° will allow a user to determine whether the second medium is air or water by reading the amount of light reflected. This will be advantageous when, for example, the first medium is the tubing (or a like structure) of a cassette for an enteral feeding.

Figure 6:
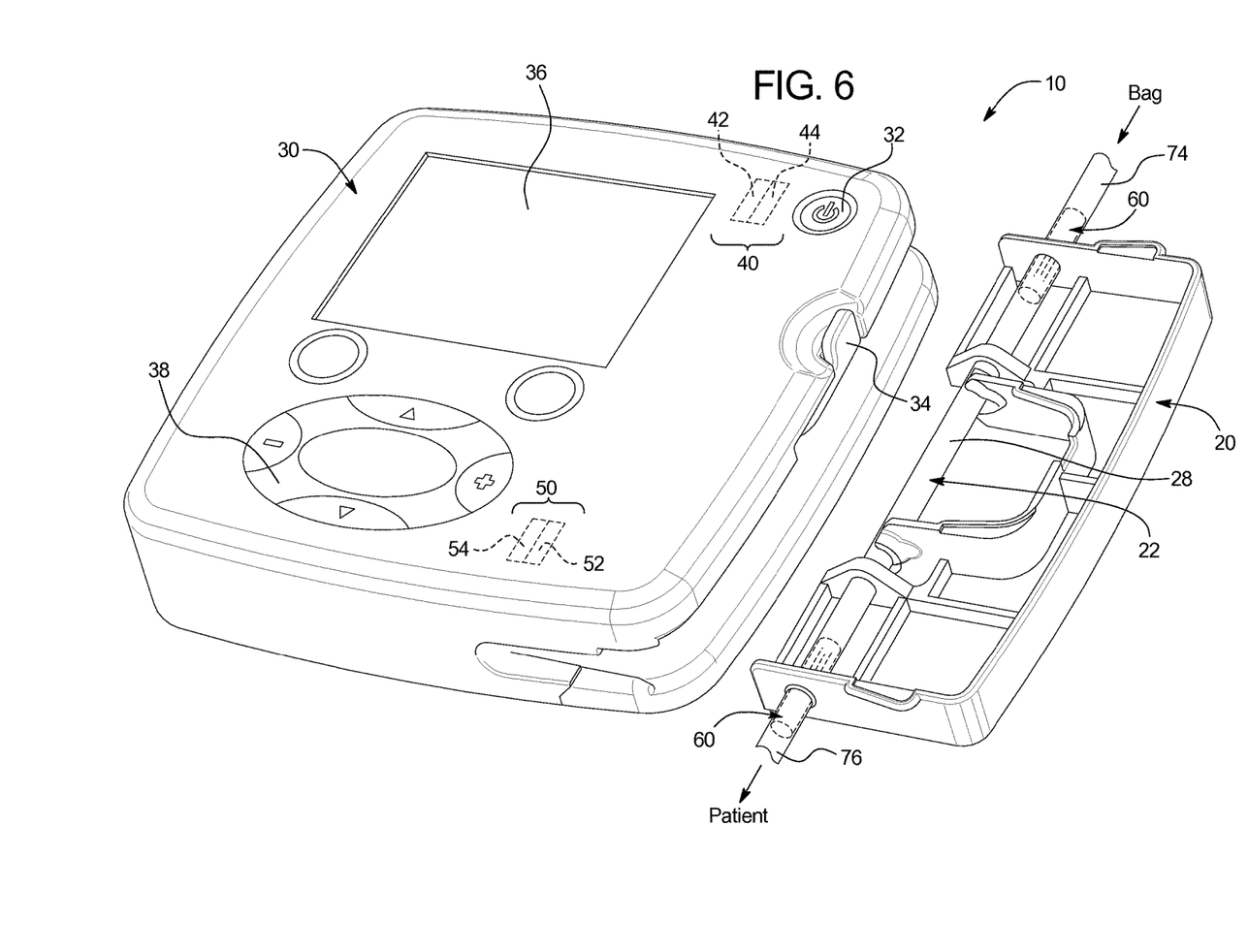
FIG. 6 shows a perspective view of a pumping device and cassette having an air-in-line sensor system in accordance with an embodiment of the present disclosure.
Figure 7:
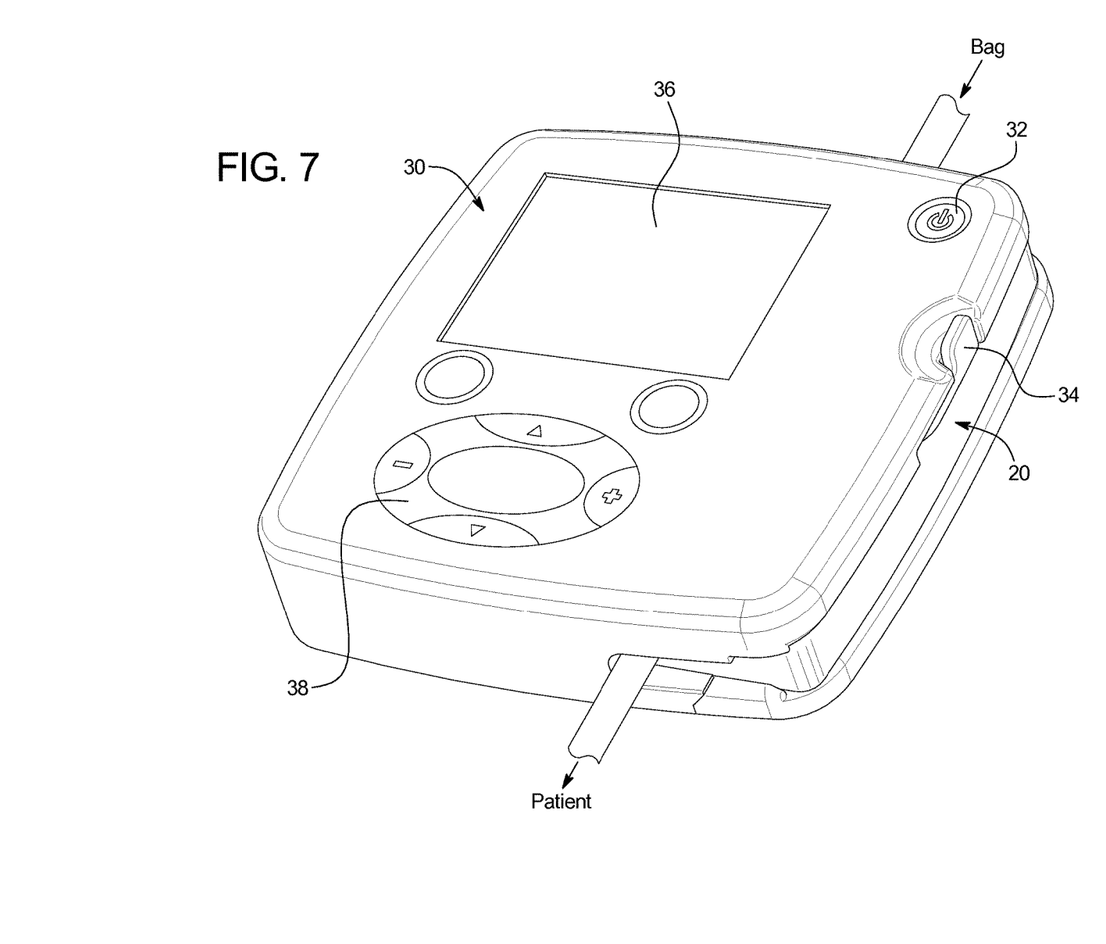
FIG. 7 shows a perspective view of the pumping device and the cassette of FIG. 6 with the cassette inserted into the pumping device in accordance with an embodiment of the present disclosure.

As illustrated in FIGS. 6-7, in an embodiment, the present disclosure provides an air-in-line sensor system 10 including a cassette 20 removably attachable to a pumping device 30. Cassette 20 can include a housing or support structure having any suitable shape such as the one shown in FIG. 6. Cassette 20 can be designed to be inserted partially or wholly within pumping device 30, as seen in FIG. 7. The design of cassette 20 can help in loading an enteral feeding tube set into pumping device 30 without having to route/guide the tubes or stretch the tubes from the tube set over a rotor (e.g., part of a peristaltic pump) contained within pumping device 30. Non-limiting examples of alternative cassette configurations are described in U.S. Pat. Nos. D504,506, D505,199, D455,489, D501,924 and D507,647, which are incorporated herein by reference. Cassette 20 can be made from any suitable rigid, semi-rigid or flexible material. Cassette 20 can also be designed such that it can be inserted into pumping device 30 only one way.

Cassette 20 includes tube 22, which can be flexible and have portions that are rigid or semi-rigid. Tube 22 can be a feeding tube and be constructed and arranged to be incorporated with the rotors of a pump (e.g. peristaltic pump) in pumping device 30.

Pumping device 30 can be an enteral feeding pump. The pump contained within pumping device 30 can be a peristaltic pump. Non-limiting examples of pumping devices are described in U.S. Pat. No. 6,659,976, which is incorporated herein by reference. As shown by FIG. 7, pumping device 30 can include a monitor/information screen 36 and a control pad 38 for operating pumping device 30. Monitor/information screen 36 and control pad 38 can also be used in conjunction with the air-in-line sensor system in embodiments of the present disclosure. Pumping device 30 can further include a power button 32 and a release mechanism 34 for releasing cassette 20 from pumping device 30.

Pumping device 30 can also include one or more infrared sensors 40 and 50. In an embodiment, pumping device 30 includes one infrared sensor 40 that is located on an inlet side of pumping device 30 where cassette 20 is connected to a solution bag, as shown in FIG. 6. Infrared sensors 40, 50 include infrared reflective light emitters 42 and 52, respectively. Infrared sensors 40, 50 further include infrared detectors 44 and 54, respectively, positioned as part of the air-in-line sensor system 10 within an inner section of pumping device 30. Infrared light emitters 42, 52 can be a light emitting diode. Infrared light detectors 44, 54 can be a photodiode or a phototransistor. Infrared sensors 40 and 50 are located in pumping device 30 to avoid wear and tear or damage to infrared sensors 40 and 50 due to handling by a user. This is important because the most expensive element of the present systems are infrared sensors 40 and 50.

Figure 8:
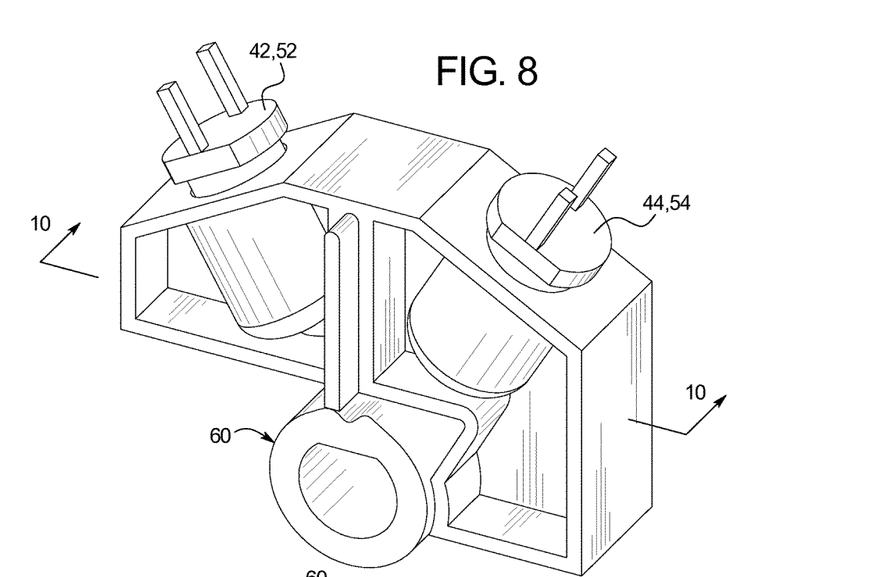
FIG. 8 shows a perspective view of an adapter and an infrared sensor having an infrared light emitter and an infrared light detector in accordance with an embodiment of the present disclosure.

Infrared sensors 40, 50 can be any suitable infrared sensor having an infrared emitting device 42 and a detection device 44, as shown by FIG. 8. Non-limiting examples of infrared sensors 40, 50 include infrared sensors developed under the QRD series by Fairchild Semiconductor. Infrared light emitters 42, 52 and infrared detectors 44, 54 can be supported or positioned on any suitable support (e.g. within pumping device 30).

Cassette 20 further includes tube 22 and at least one adapter 60 as part of the air-in-line sensor system, and as shown in FIG. 6. When cassette 20 is inserted into pumping device 30, infrared reflective light emitters 42, 52 and infrared detectors 44, 54 can be positioned to lay side-by-side and adjacent to adapter 60, as illustrated in FIG. 8. In this manner, although infrared sensors 40, 50 are illustrated in FIG. 6 as being located on a top, interior portion of pumping device 30, so as to be located on a top portion of cassette 20, infrared sensors 40, 50 may also be located on a bottom, interior portion of pumping device 30, so as to be located on a bottom portion of cassette 20 when cassette 20 is loaded into pumping device 30, as shown in FIG. 7. In an embodiment, infrared sensors 40, 50 are located on a bottom, interior portion of pumping device 30 so as to emit infrared light from infrared reflective light emitters 42, 52 in an upward direction to contact a portion of adapter 60, which reflects (and/or refracts) the infrared light in a downward direction to be received by infrared detectors 44, 54.

Figures 9, 10:
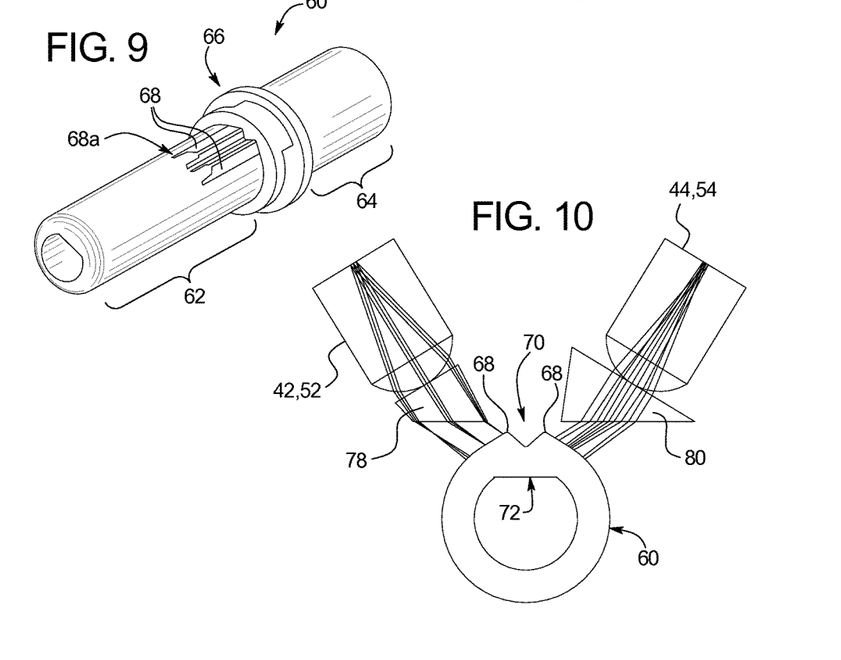
FIG. 9 shows a perspective view of an adapter for use with an air-in-line sensor system in accordance with an embodiment of the present disclosure.
FIG. 10 shows a cross-sectional view of the adapter and infrared sensor of FIG. 8 along line 10-10 in accordance with an embodiment of the present disclosure.

As is most clearly shown in FIG. 9, adapter 60 has a first portion 62 and a second portion 64 separated by an intermediate third portion 66. First portion 62 includes two wedge-shaped projections 68 that extend from the natural surface of first portion 62. In other words, as illustrated in FIG. 9, adapter 60 is substantially cylindrically shaped (having a natural cylindrically shaped surface) and wedge-shaped projections 68 extend from what would be a cylindrically shaped surface underneath wedge-shaped projections 68 if wedge-shaped projections 68 were not included on adapter 60. Although illustrated as substantially cylindrical in FIG. 9, the skilled artisan will appreciate that adapter 60 may have any shape known in the art that allows adapter 60 to function as a tubing adapter.

Wedge-shaped projections 68 are substantially triangularly shaped defining a substantially triangularly shaped recess 70 therebetween. Flat portions of wedge-shaped projections 68 opposite recess 70 may be used as surfaces for transmission of incident infrared light rays and for reflected infrared light rays, as shown in FIG. 10. In this manner, and in an embodiment, infrared reflective light emitters 42, 52 can emit infrared light, which may be focused by a lens (e.g., prism) 78 prior to transmission through the material of adapter 60 to an interior wall 72 of adapter 60, which serves as the media separation surface between adapter 60 and the contents flowing through adapter 60 and tube 22 of the enteral feeding system (e.g., nutritional composition, water, air, etc.). When the infrared light hits media separation surface 72, the incident infrared light ray is reflected and/or refracted. Any reflected light is reflected through adapter 60, which may be focused by a lens (e.g., prism) 80 prior to reception of the infrared light rays by infrared detectors 44, 54. For ease and accuracy of measurement of reflected and/or refracted infrared light, interior wall 72 of adapter 60 should be substantially perpendicular to a line running through the middle of recess 70 and bisecting adapter 60 into two equal halves. A remaining portion of the interior wall of adapter 60 can be substantially cylindrical for ease of passing fluid therethrough.

With respect to prisms 78, 80, the skilled artisan will appreciate that alternative embodiments are provided in the present disclosure that do not include prisms 78, 80. For example, in an embodiment, prisms 78, 80 of FIG. 10 are not included. Instead, the relative angles of the infrared reflective light emitters 42, 52 and infrared detectors 44, 54 may be increased. By removing prisms 78, 80 and increasing the relative angles of infrared reflective light emitters 42, 52 and infrared detectors 44, 54, it is possible to manufacture a cheaper infrared sensor 40, 50 and to avoid any possible issues that may arise from use of prisms 78, 80 (e.g., imperfections that cause reflection or refraction issues).

In another embodiment, at least a portion of the interior surface of the adapter may be infrared transmissive. For example, the interior surface may be infrared transmissive, specifically over a range of incident light angles, such that the interface between the surface and the fluid or air bolus in the adaptor changes the range of those angles. Wedge-shaped projections 68 or any portion of the adapter 60 may be infrared transmissive depending on the range of incident light angles desired and/or the type of fluid or air bolus flowing through adapter 60. Infrared light that is emitted by any of the light emitters described herein can pass through the interior surface, reflect off of the fluid or air bolus, and be sensed by any of the infrared detectors as described herein.

In an embodiment, wedge-shaped projections 68 may have a sloped portion 68a toward a front end of adapter 60, as shown in FIG. 9. Sloped portions 68a of wedge-shaped projections 68 may assist a user in press-fitting tube 22 around adapter 68 for use in pumping fluids through adapter 60. Sloped portions 68a may also serve as a stopping means to prevent tube 22 from extending the entire length of first portion 62. In other words, one advantage of the use of present adapter 60 is that infrared light does not need to travel through tube 22 and adapter 60 to arrive at media separation surface 72. Instead, infrared light simply has to pass through adapter 60 to arrive at media separation surface 72.

Second portion 64 of adapter 60 is so constructed and arranged to be attached to a tubing portion 74 that is connected to a nutritional composition supply bag, and/or a tubing portion 76 that is connected to a patient for fluid delivery. Second portion 64 may be attached to tubing portions 74, 76 by any means known in the art including, but not limited to, press-fitting, bonding, welding, adhesives, etc. In an embodiment, second portion 64 is bonded to tubing portions 74, 76. Second portion 64 may have a diameter that is smaller than, the same as, or greater than first portion 62. In an embodiment, second portion 64 has a diameter that is greater than first portion 62.

Third portion 66 is located intermediate first portion 62 and second portion 64, and has a diameter that is greater than first portion 62 and second portion 64. Third portion 66 is useful for proper alignment and placement of adapter 60 in cassette 20. As shown in FIG. 6, adapter 60 is located on outer edges of cassette 20 and may be placed therein by inserting first portion 62 of adapter 60 into a similarly sized hole in cassette 20 and press-fitting first portion 62 of adapter 60 into tube 22. In this manner, third portion 66 prevents adapter 60 from being inserted too far into an interior portion of cassette 20 and helps to keep tubing 22, 74, 76 in place during delivery of fluids to a patient.

As is shown in FIG. 9, and as discussed in part above, adapter 60 has a special geometry including at least wedge-shaped projections 68 and interior wall 72 that has been adopted to take advantage of the physical principles used to detect air in the tubing set and to solve mold-ability issues. Not only is the geometry of adapter 60 advantageous, however, but the material used to manufacture adapter 60 is also beneficial. In an embodiment, adapter 60 may be manufactured from a food grade polymer such as, but not limited to polypropylene, Teflon®, methylmethacrylate-acrylonitrile-butadiene-styrene copolymer ("MABS"), etc. In an embodiment, adapter 60 is made of polypropylene, which is well-suited for use with foods and has a low adhesion coefficient. By preventing food from sticking to an interior of adapter 60, a greater amount of infrared light is allowed to pass therethrough, and materials having increased viscosities may also be used.

Referring now to FIG. 10, infrared reflective light emitter 42, 52 sends a beam of light to a section of adapter 60, which is attached to cassette 20 and receives the nutritional composition from the bag from one side and interfaces with the patient on the other. The food or the air passing through adapter 60 and, hence, tube 22, will cause a different amount of light be transferred to detector 44, 54 placed at the reflection angle. An LED driving circuit and a photosensor amplifier and filter circuits will send an output to an analog to digital converter, which will allow a pump microcontroller to supply the optimal amount of infrared light and to determine the presence of air in adapter 60 and, hence, tube 22, instead of nutrient fluid.

As mentioned briefly above, fluid can flow through tube 22 in the direction from the bag to the patient as shown in FIG. 6. Tube 22 extends within the bound of cassette 20. Adapter 60 is used to join tube 22 with tube 74 that attaches to the bag containing a nutritional composition source. Similarly, adapter 60 is used to join tube 22 with tube 76 that attaches to the person receiving the nutritional composition. In this manner, tube 22 may be press fit over first portion 62 of adapter 60 until tube 22 is sealingly joined to adapter 60. In an embodiment wherein two adapters 60 are present, tube 22 is joined to adapters 60 at both ends of cassette 20.

Infrared sensors 40 and 50 can be positioned on either side of a pump (not shown) within pumping device 30. For example, the pump can be located at a central location of pumping device 30 and would interact with tube 22 located at a central cut-out portion 28 of cassette 20. Accordingly, infrared sensor 40 may be placed upstream of the pump at a location to interact with adapter 60 located upstream of the pump (e.g., receive a nutritional composition from a container or bag). Similarly, infrared sensor 50 may be placed downstream of the pump at a location to interact with adapter 60 located downstream of the pump (e.g., sending a nutritional composition to the patient). Similarly, both infrared sensors 40, 50 may be included in an embodiment, one infrared sensor 40 may be included in another embodiment, or one infrared sensor 50 may be included in yet another embodiment.

During operation, the pump (not shown) within pumping device 30 located near portion 28 pumps the nutritional composition from a bag through cassette 20 via tube 74, a first adapter 60, tube 22, a second adapter 60, and tube 76 to a patient. If there is no air detected in the line between the bag and the pump or the pump and the patient, pumping device 30 will continue to deliver a feeding to the patient. However, if air is detected by sensor system 10 at either first or second adapters 60, infrared sensors 40, 50 send this information to a central processing unit of pumping device 30, which is able to use stored information and parameters to determine how much air has been sensed in the line between the bag and the patient. If a predetermined threshold of an amount of air in the tubing is detected, air-in-line sensor system 10 may enter a safe mode where an alarm is sounded to warn the patient, or the pumping device 30 automatically shuts off to cease delivery of the fluid, etc.

In another embodiment, pumping device 30 may have a clear window (not shown) located on an interior surface. The window can be made, for example, from a molded, plastic and can serve as a barrier between infrared sensors 40, 50 and any exterior source of liquid. The window may be chemically doped and can be an infrared transparent/transmissive surface so that infrared light can pass though the window. The purpose of the window is to prevent liquid from entering an interior portion of pumping device 30 that contains the electrical and mechanical components. For example, during cleaning of pumping device 30, it is desirable to prevent water, soap and/or cleaning chemicals from leaking into pumping device 30 and damaging or destroying any electrical or mechanical components.

In another embodiment, the infrared light emitted from an infrared light emitter may be either pulsed or continuous. An advantage of providing a continuous emission of infrared light includes a constant monitoring (e.g., detecting) of any fluids being pumped through a cassette and provided to a patient. In this manner, continuous detection reduces any possibility of failing to detect a problematic pumping condition (e.g., air bubbles). There are also several advantages, however, to providing an embodiment wherein the infrared light is pulsed. For example, pulsed infrared light detection provides for ambient light rejection capability, stability of the amount of infrared emitted light (e.g., emitter does not over-heat), longer life of the emitter, which will not degrade its optical characteristics for aging, and reduced power consumption. As such, the skilled artisan will appreciate that the presently disclosed pumps and pumping systems may include either pulsed or continuous infrared light emissions.

In an alternative embodiment, the present disclosure provides a cassette that incorporates an infrared reflective sensor including an infrared light emitter and an infrared detector. In this regard, the pumping device does not house the infrared reflective sensor. However, the infrared reflective sensor on the cassette can be constructed and arranged to interact with the pumping device so that the results of the infrared reflective sensor can be displayed on a monitor of the pumping device.

In yet another embodiment, the present disclosure provides a method of detecting air in a tubing for an enteral feeding system. The method comprises providing an air-in-line sensing system including a feeding tube and an infrared reflective sensor including an infrared light emitter and an infrared light detector. The feeding tube can be incorporated as part of a cassette that can be attached to a pumping device of the enteral feeding system.

The method further comprises detecting air within the feeding tube by transmitting an infrared light toward an adapter in fluid communication with the feeding tube and detecting reflected infrared light using the infrared detector, for example, based on an amount of light reflected and/or refracted. If air is detected in the feeding tube, the pumping device can be stopped, for example, during an enteral feeding cycle.

Applicants have combined a unique adapter with an air-in-line sensor system to be able to determine whether the adapter and/or tubing of an enteral feeding system contains a fluid or air. Attempts to adopt the above physical principles to implement such an air-in-line sensor for an enteral feeding pump was not easily accomplished, however. In this manner, Applicants were cognizant of the following potential complications: (i) the physical dimensions of the pump did not allow a large reflection surface; (ii) the costs of the sensor were not to limit its commercialization; (iii) the light source could not be a collimated X-ray, therefore, secondary level optical phenomenon was considered; (iv) not all of the light in the pump was reflected or refracted, and absorption and scattering of light was also considered; (v) ambient light can affect the photosensor reading; (vi) some foods show high viscosity and are not homogeneous, which can create tubes clearance issues; (vii) most of the food materials with a high degree of clearance had very low refraction indices, which resulted in bonding and slippery problems interfacing with the tubes; (viii) consistent mold-ability of optical parts with lens was difficult; (ix) spread in the opto/electrical parameters of the optical components was typically high; and (x) aging of the optical components could effect sensor sensibility.

By working through the difficulties in achieving the present air-in-line sensors, Applicants were able to achieve an improved air-in-line sensor that provides many advantages over prior art air sensors. For example, the present air-in-line sensors are a low cost, reliable solution that works in several operating environments. The present air-in-line sensors continue to work regardless of whether the tube is occluded, and do not require any plate against which light is reflected or absorbed. The air-in-line sensors of the present disclosure also operate with large varieties of foods and are immune against aging and associated problems typically found with similar optical systems.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An adapter device comprising:
    first and second cylindrical portions defining a fluid flow channel, the first cylindrical portion comprising two adjacent wedge-shaped protrusions, each wedge-shaped protrusion having at least a portion that is infrared transmissive and each wedge-shaped protrusion defining an outer surface and an inner surface, the fluid flow channel extends through both of the first and second cylindrical portions, and a portion of the inner surface is infrared transmissive.

2. The adapter device of claim 1, wherein the inner surfaces of the two adjacent wedge-shaped protrusions define a substantially triangularly shaped recess.

3. The adapter device of claim 1, wherein the adapter is manufactured from polypropylene.

4. The adapter device of claim 1, wherein the two adjacent wedge-shaped protrusions are substantially triangle-shaped and define a substantially triangle-shaped recess therebetween, an interior wall of the first cylindrical portion is substantially perpendicular to a line running through a middle of the recess and bisecting the adaptor device into two equal halves, and the interior wall of the first cylindrical portion is a media separation surface between the adapter device and contents flowing through the adapter device.

5. A cassette comprising:
    a rigid frame;
    a tube; and
    at least one adapter comprising first and second cylindrical portions defining a fluid flow channel, the first cylindrical portion comprising two adjacent wedge-shaped protrusions, each wedge-shaped protrusion having at least a portion that is infrared transmissive and each wedge-shaped protrusion defining an outer surface and an inner surface, the fluid flow channel extends through both of the first and second cylindrical portions, and a portion of the inner surface is infrared transmissive.

6. The cassette of claim 5, wherein the at least one adapter is located on an end of the cassette.

7. The cassette of claim 5, wherein the first cylindrical portion of the at least one adapter is so constructed and arranged to mate with the tube.

8. The cassette of claim 5, wherein the second cylindrical portion of the at least one adapter is so constructed and arranged to mate with a second tube.

9. The cassette of claim 5, the at least one adapter comprises a first adapter and a second adapter, the first adapter located on a first end of the cassette and the second adapter located on a second end of the cassette.

10. A sensor system comprising:
    a pumping device comprising at least one infrared reflective sensor having an infrared light emitter and an infrared detector; and a cassette removably attached to the pumping device, the cassette comprising a tube and at least one adapter comprising a first hollow cylindrical portion and a second hollow cylindrical portion defining a fluid flow channel, the first hollow cylindrical portion comprising first and second adjacent wedge-shaped protrusions, each wedge-shaped protrusion having at least a portion that is infrared transmissive and each wedge-shaped protrusion defining an outer surface and an inner surface, the fluid flow channel extends through both of the first and second hollow cylindrical portions, and a portion of the inner surface is infrared transmissive, wherein the infrared reflective sensor is positioned so that an infrared light can be transmitted through the outer surface of the first wedge-shaped protrusion and at least a portion of the infrared light reflected off an inner surface of the first hollow cylindrical portion can be detected by the infrared detector.

11. The sensor system of claim 10, wherein the pumping device is an enteral feeding pump.

12. The sensor system of claim 10, wherein the infrared light emitter and the infrared detector are positioned on the same side within the pumping device.

13. The sensor system of claim 10, wherein the infrared light emitter and the infrared detector are located on a bottom, interior portion of the pumping device such that the infrared light emitter emits the infrared light in an upward direction.

14. The sensor system of claim 13, wherein the at least one adapter is located on an end of the cassette and is configured such that the first and second adjacent wedge-shaped protrusions are oriented downward to communicate with the infrared light emitter and the infrared detector.

15. A method of detecting air in a tubing set for an enteral feeding system, the method comprising the steps of:

providing a cassette having an adapter sealingly attached to an enteral feeding tube, the adapter comprising a first hollow cylindrical portion and a second hollow cylindrical portion defining a fluid flow channel, the first hollow cylindrical portion comprising a first wedge-shaped protrusion adjacent to a second wedge-shaped protrusion, each of the first and second wedge-shaped protrusions having at least a portion that is infrared transmissive and each of the first and second wedge-shaped protrusions defining an outer surface and an inner surface, the fluid flow channel extends through both of the first hollow cylindrical portion and the second hollow cylindrical portion, and a portion of the inner surface is infrared transmissive; and detecting air within the enteral feeding tube by transmitting an infrared light to the outer surface of the first wedge-shaped protrusion and detecting an amount of reflected infrared light using a detector.

16. The method of claim 15, wherein the infrared light is transmitted through the outer surface of the first wedge-shaped protrusion, at least partially reflected off an interior wall of the first hollow cylindrical portion, and subsequently the reflected infrared light passes through the outer surface of the second wedge-shaped protrusion.

17. The method of claim 15 further comprising inserting the cassette into a pumping device to administer an enteral feeding to a patient.

18. The method of claim 15 further comprising stopping an enteral feeding cycle if air is detected in the enteral feeding tube.

19. The method of claim 15 further comprising sounding an audible alarm if a threshold amount of air is detected in the enteral feeding tube.

* * * * *

UNITED STATES PATENT AND TRADEMARK OFFICE
CERTIFICATE OF CORRECTION

Page 1 of 1

PATENT NO. : 9,770,552 B2
APPLICATION NO. : 14/234768
DATED : September 26, 2017
INVENTOR(S) : Adam Hartman, Paul Nguyen and David Charles Cummings It is certified that error appears in the above-identified patent and that said Letters Patent is hereby corrected as shown below:

On the Title Page

Insert:
--(60) Related U.S. Application Data
Continuation of application No. 13/190,155, filed on Jul. 25, 2011, now Pat. No. 9,033,923--

Signed and Sealed this
Sixteenth Day of January, 2018

Joseph Matal
*Performing the Functions and Duties of the*
*Under Secretary of Commerce for Intellectual Property and*
*Director of the United States Patent and Trademark Office*